(12) United States Patent
Laitinen et al.

(10) Patent No.: US 8,744,269 B2
(45) Date of Patent: Jun. 3, 2014

(54) OPTICAL MEASUREMENT INSTRUMENT WITH DATA TRANSMISSION

(75) Inventors: Jyrki Laitinen, Kuusisto (FI); Antero Yli-Koski, Kaarina (FI); Markku Ojala, Turku (FI)

(73) Assignee: Wallac Oy, Turku (FI)

( * ) Notice: Subject to any disclaimer, the term of this patent is extended or adjusted under 35 U.S.C. 154(b) by 506 days.

(21) Appl. No.: 13/146,271

(22) PCT Filed: Jan. 18, 2010

(86) PCT No.: PCT/FI2010/050023
§ 371 (c)(1),
(2), (4) Date: Sep. 20, 2011

(87) PCT Pub. No.: WO2010/084245
PCT Pub. Date: Jul. 29, 2010

(65) Prior Publication Data
US 2012/0002960 A1   Jan. 5, 2012

Related U.S. Application Data

(60) Provisional application No. 61/149,549, filed on Feb. 3, 2009.

(30) Foreign Application Priority Data

Jan. 26, 2009   (FI) ..................... 20095063

(51) Int. Cl.
*H04B 10/00*   (2013.01)
(52) U.S. Cl.
USPC ........... 398/140; 398/151; 398/154; 398/166; 398/25
(58) Field of Classification Search
USPC ............ 398/140, 151, 154, 165, 166, 135, 25
See application file for complete search history.

(56) References Cited

U.S. PATENT DOCUMENTS

| 5,039,219 A | 8/1991 | James et al. |
| 5,428,470 A | 6/1995 | Labriola, II |

(Continued)

FOREIGN PATENT DOCUMENTS

| DE | 197 03 854 A1 | 8/1998 |
| DE | 298 09 721 U1 | 12/1998 |

(Continued)

OTHER PUBLICATIONS

Finnish Search Report, dated Oct. 28, 2009, from corresponding Finnish application.

(Continued)

*Primary Examiner* — Daniel Washburn
*Assistant Examiner* — Hibret Woldekidan
(74) *Attorney, Agent, or Firm* — Young & Thompson (57) ABSTRACT

An optical measurement instrument comprises operational modules (101-107) that are interconnected via a digital communication network (110). Each operational module comprises a transceiver (111-117) connected to the digital communication network and arranged to support a pre-determined digital communication protocol employed in the digital communication network. Those operational modules that include a detector further comprise an analog-to-digital converter (118) for converting a detected signal into a digital form and a digital circuitry (119) for providing digital information based on the detected signal with address data related to a particular operational module to which the digital information is to be delivered via the digital communication network. As information is transferred between operational modules via the digital communication network using the pre-determined digital communication protocol, the operational modules can be tested independently of each other using a test bench system arranged to support the pre-determined digital communication protocol.

13 Claims, 4 Drawing Sheets

(56) References Cited

U.S. PATENT DOCUMENTS

| | | | |
|---|---|---|---|
| 5,761,431 A * | 6/1998 | Gross et al. | 709/225 |
| 5,843,692 A * | 12/1998 | Phillips et al. | 435/14 |
| 5,985,214 A | 11/1999 | Stylli et al. | |
| 6,097,025 A | 8/2000 | Modlin et al. | |
| 6,122,042 A * | 9/2000 | Wunderman et al. | 356/73 |
| 6,535,528 B1 | 3/2003 | Rhodes et al. | |
| 6,538,728 B1 | 3/2003 | Stolle et al. | |
| 6,875,977 B2 * | 4/2005 | Wolter et al. | 250/221 |
| 6,952,263 B2 * | 10/2005 | Weiss et al. | 356/425 |
| 6,977,722 B2 | 12/2005 | Wohlstadter et al. | |
| 7,515,260 B2 * | 4/2009 | Hagler | 356/310 |
| 8,098,995 B2 * | 1/2012 | Otani et al. | 398/154 |
| 8,542,349 B2 * | 9/2013 | Laitinen et al. | 356/32 |
| 2001/0045358 A1 | 11/2001 | Kopf-Sill et al. | |
| 2004/0057870 A1 * | 3/2004 | Isaksson et al. | 422/52 |
| 2005/0062969 A1 * | 3/2005 | Harju et al. | 356/417 |
| 2007/0109530 A1 | 5/2007 | Ueno et al. | |
| 2008/0044879 A1 | 2/2008 | Harjes et al. | |
| 2008/0100822 A1 * | 5/2008 | Munro | 356/4.01 |
| 2008/0212960 A1 * | 9/2008 | Lundquist et al. | 398/25 |
| 2008/0240321 A1 | 10/2008 | Narus et al. | |
| 2008/0247764 A1 * | 10/2008 | Lewin et al. | 398/154 |
| 2009/0305392 A1 | 12/2009 | Alfredsson et al. | |
| 2010/0191418 A1 * | 7/2010 | Mimeault et al. | 701/36 |
| 2010/0203573 A1 * | 8/2010 | Heinonen et al. | 435/29 |
| 2010/0252748 A1 * | 10/2010 | Laitinen et al. | 250/458.1 |
| 2012/0001089 A1 * | 1/2012 | Laitinen | 250/458.1 |
| 2012/0057164 A1 * | 3/2012 | Tezuka et al. | 356/445 |
| 2013/0004157 A1 * | 1/2013 | Hakim | 398/25 |

FOREIGN PATENT DOCUMENTS

| | | |
|---|---|---|
| DE | 10 2007 020 440 A1 | 10/2008 |
| EP | 1 575 201 A1 | 9/2005 |
| EP | 1 882 948 A2 | 1/2008 |
| JP | 6097893 A | 4/1994 |

OTHER PUBLICATIONS

International Search Report, dated Jun. 14, 2010, from corresponding PCT application.

* cited by examiner

OPTICAL MEASUREMENT INSTRUMENT WITH DATA TRANSMISSION

FIELD OF THE INVENTION

The invention relates to method for transferring information between operational modules of an optical measurement instrument. An optical measurement can be, for example but not necessarily, an absorption measurement, a photoluminescence measurement, or a chemiluminescence measurement. Furthermore, the invention relates to an optical measurement instrument and to an operational module for an optical measurement instrument.

BACKGROUND

The work in analytical biochemical laboratories and in clinical laboratories is often based on different tags or labels coupled on macromolecules under inspection. Typical labels used are different radioactive isotopes, enzymes, different fluorescent molecules and e.g. fluorescent chelates of rare earth metals. Detection of enzyme labels can be performed by utilizing its natural biochemical function, i.e. to alter the physical properties of molecules. In enzyme immunoassays colourless substances are catalysed by enzyme to colourful substances or non-fluorescent substances to fluorescent substances.

The colourful substances can be measured with absorption measurement, i.e. photometric measurement. In the absorption measurement the intensity of filtered and stabilized beam is first measured without any sample and then the sample inside one plate is measured. The absorbance i.e. the absorption values are then calculated.

The fluorescent substances can be measured with fluorescent measurement that is generally used for measuring quantities of fluorescent label substance in a sample. The most photoluminescence labels are based on molecular photoluminescence process. In this process optical radiation is absorbed by the ground state of a molecule. Due to the absorption of energy the quantum molecule rises into higher excited state. After the fast vibrational relaxation the molecule returns back to its ground state and the excess energy is released as an optical quantum. Due to losses in this process the average absorbed energies are higher than the average emitted energies.

A further measurement method is chemiluminescence measurement where emission of a substance is measured from a sample without excitation by illumination. Thus a photoluminometer suitable for photoluminescence measurements can also be used as a chemiluminometer.

Further, there is an analysing method called Amplified Luminescent Proximity Homogeneous Assay or AlphaScreen™. The function of the AlphaScreen™ method is based on the use of small beads that attach to the molecules under study. There are two types of beads that are coated with a material acting either as a donor or acceptor of singlet-state oxygen. The measurement starts, when the liquid sample is illuminated by light with a suitable wavelength e.g. 680 nm. After this, the material in the donor bead converts ambient oxygen into singlet-state oxygen. The single-state molecules have a short lifetime and they can reach only about a 200 nm distance by diffusion in the liquid. If the chemical reaction in question has taken place, both the donor and acceptor beads are bound to the same molecule and so they are sufficiently close to each other. In this case the singlet-state oxygen may reach the acceptor bead where a series of reactions is started. As the last phase of the reaction the coating material in the acceptor beads emits photons in the 500-700 nm range. If the chemical reaction has not taken place the singlet-state oxygen cannot reach the acceptor bead and the emission light is not detected. By measuring the intensity of light it is possible to conclude the efficiency of the chemical reaction.

An optical measurement instrument suitable for performing some or all of the measurements of the kind described above comprises typically at least one excitation light source for producing excitation beams to one or more samples to be measured at each time. Each excitation light source can be for example a flash lamp or a laser source. An optical path from an excitation light source to a sample may contain for example lenses, fibers, mirrors, dichroic mirrors, optical filters, monochromators and/or other optical elements. The optical measurement instrument further comprises at least one detector for detecting emission beams emitted by the samples to be measured at each time, and for producing detection signals responsive to the detected emission beams. Each detector can be for example a photodiode or a photo-multiplier tube. An optical path from the sample to the detector may contain for example lenses, fibers, mirrors, dichroic mirrors, optical filters, monochromators, and/or other optical elements. Each sample to be measured is stored in one of a plurality of sample wells that are built on a sample plate, e.g. a microtitration plate. The optical measurement instrument may comprise, for example, a movable sledge adapted to receive the sample plate. Due to the fact that the sample plate is movable, the samples can be measured in a temporally successive manner so that each sample is in turn the sample that is currently being measured. The optical measurement instrument may further comprise a processing device for producing a measurement result for each sample to be measured on the basis of the detection signal related to that sample.

An optical measurement instrument of the kind described above is a complicated apparatus from the viewpoints of manufacturing, testing, and outsourcing the manufacturing and/or testing. This causes a need to modularize the structure of an optical measurement instrument so that the optical measurement instrument can be assembled of different operational modules such as, for example, an excitation light source module, an excitation monocromator module, a sample track module arranged to hold and move a sample plate, an emission monocromator module, and a detector module. Publication U.S. Pat. No. 6,977,722 discloses an example of an optical measurement instrument having a modular structure. A challenge related to the modularization is that the operational modules should be able to be manufactured and tested sufficiently independently of each other in order that the modular structure would provide the desired advantages.

SUMMARY

In accordance with a first aspect of the invention, there is provided a new optical measurement instrument comprising operational modules. At least one of the said operational modules includes an excitation light source arranged to produce an excitation beam for at least one of samples to be measured, and at least one of the said operational modules includes a detector arranged to detect an emission beam emitted by one of the samples to be measured and to produce a detection signal responsive to the detected emission beam. The optical measurement instrument according to the invention further comprises at least a part of a digital communication network arranged to support a pre-determined digital communication protocol, and each of the operational modules comprises a transceiver arranged to support the digital communication protocol and connected to the digital communication network. The at least one operational module that includes a detector further comprises an analog-to-digital converter arranged to convert the detection signal into a digital form and a digital circuitry arranged to provide digital information based on the detection signal with identifier data arranged to identify, in accordance with the digital communication protocol, from among the operational modules the particular operational module to which the digital information is to be delivered via the digital communication network. The optical measurement instrument further comprises another digital communication network and at least two of the operational modules comprise another transceiver connected to the other digital communication network for transferring synchronization messages between the at least two operational modules.

The digital communication network can be, for example, a Controller Area Network (CAN).

As the operational modules are arranged to communicate with each other via the digital communication network using the pre-determined digital communication protocol, the operational modules can be tested independently of each other using an appropriate external system arranged to support the pre-determined digital communication protocol and to operate as a test bench. This makes, for example, easier to outsource the manufacturing and/or testing of the operational modules.

In accordance with a second aspect of the invention, there is provided a new operational module for an optical measurement instrument. The operational module according to the invention comprises:
- a detector arranged to detect an emission beam emitted by one of samples to be measured and to produce a detection signal responsive to the detected emission beam,
- an analog-to-digital converter arranged to convert the detection signal into a digital form,
- a digital circuitry arranged to provide digital information based on the detection signal with identifier data arranged to identify, in accordance with a pre-determined digital communication protocol, another operational module to which the digital information is to be delivered,
- a transceiver arranged to transmit, according to the pre-determined digital communication protocol, the digital information provided with the identifier data, and
- another transceiver for transferring and receiving synchronization messages to and from other operational modules.

In accordance with a third aspect of the invention, there is provided a new method for transferring information between operational modules of an optical measurement instrument, at least one of the operational modules including an excitation light source arranged to produce an excitation beam for at least one of samples to be measured, and at least one of the operational modules including a detector arranged to detect an emission beam emitted by one of the samples to be measured and to produce a detection signal responsive to the detected emission beam. The method according to the invention comprises the following actions in the at least one operational module in which the detection signal is produced:
- converting the detection signal into a digital form,
- providing digital information based on the detection signal with identifier data that identifies, in accordance with a pre-determined digital communication protocol, from among the operational modules the particular operational module to which the digital information is to be delivered, and
- transmitting the digital information provided with the identifier data to a digital communication network connected to the operational modules and arranged to support the pre-determined digital communication protocol.

The method further comprises transferring a synchronization message from one of the operational modules to another of the operational modules using another communication network connected to the operational modules.

A number of exemplifying embodiments of the invention are described in accompanied dependent claims.

Various exemplifying embodiments of the invention both as to constructions and to methods of operation, together with additional objects and advantages thereof, will be best understood from the following description of specific exemplifying embodiments when read in connection with the accompanying drawings.

The verb "to comprise" is used in this document as an open limitation that does not exclude the existence of also unrecited features. The features recited in depending claims are mutually freely combinable unless otherwise explicitly stated.

BRIEF DESCRIPTION OF THE FIGURES

The exemplifying embodiments of the invention and their advantages are explained in greater detail below in the sense of examples and with reference to the accompanying drawings, in which.

DESCRIPTION OF THE EMBODIMENTS

Figure 1:
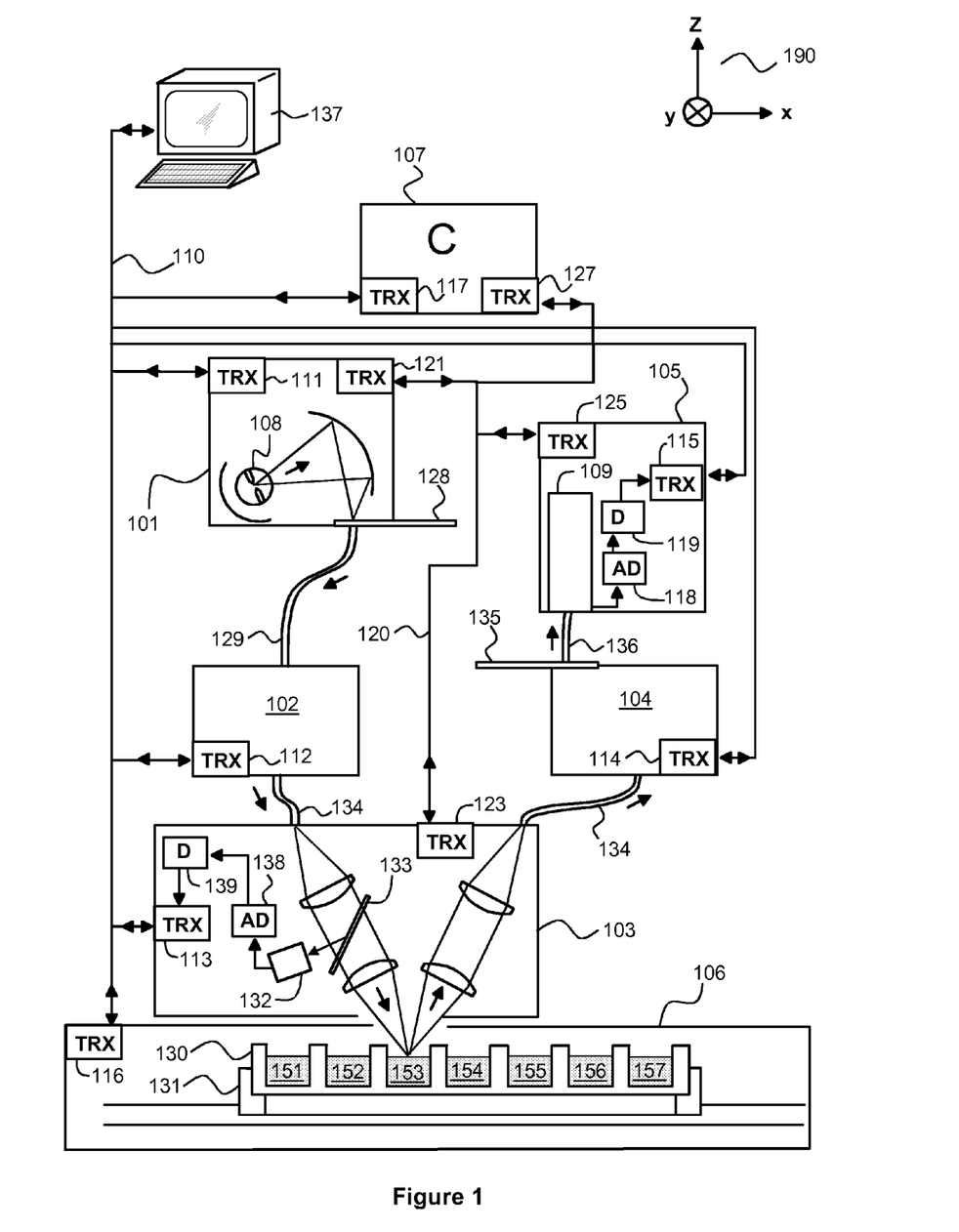
FIG. 1 shows a schematic illustration of an optical measurement instrument according to an embodiment of the invention.

FIG. 1 shows a schematic illustration of an exemplifying optical measurement instrument according to an embodiment of the invention. The optical measurement instrument is suitable for e.g. photoluminescence and chemiluminescence measurements and it comprises the following operational modules: an excitation light source module 101, an excitation monocromator module 102, a measurement head module 103, a sample track module 106, an emission monocromator module 104, a detector module 105, and a control module 107. A more detailed description of the above-mentioned operational modules 101-107 is given later in this document. The optical measurement instrument comprises at least a part of a digital communication network 110 arranged to support a pre-determined digital communication protocol. The digital communication network 110 may extend outside the optical measurement instrument for example to an external control and/or monitoring system 137. The digital communication network 110 can be any suitable digital communication network which enables the operational modules 101-107 to transfer digital information between each other and to and from a possible external control and/or monitoring system 137. The digital communication network 110 is preferably a Controller Area Network (CAN) versions of which can be found in technical specifications SAE J1939 (Society of Automotive Engineers) and ISO 11898 (International Organization for Standardization) but it is also possible to use some other network technologies such as Ethernet. A description of Ethernet can be found e.g. in the technical specification IEEE 802.3 (Institute of Electrical and Electronics Engineers).

Samples 151, 152, 153, 154, 155, 156, 157 to be measured are stored in sample wells that are built on a sample plate 130, e.g. a microtitration plate. The sample track module 106 comprises a sledge 131 that is adapted to receive the sample plate 130 and is movable in the xy-plane defined by a co-ordinate system 190. Due to the fact that the sample plate is movable, the samples can be measured in a temporally successive manner so that each sample is in turn the sample that is currently being measured. The sample track module 106 comprises a transceiver 116 connected to the digital communication network 110 and arranged to support the digital communication protocol used in the digital communication network. The digital communication network can be used for transferring control and monitoring data to and from the sample track module 106. The control and monitoring data can relate, for example, to the position of the sledge 131 and/or to temperature measured in the sample track module.

The excitation light source module 101 comprises an excitation light source 108 that can be for example a flash lamp such as a xenon flash lamp. The excitation light produced by the excitation light source is focused with a concave mirror to an optical filter wheel 128. The optical filter wheel may comprise both optical filters and mere apertures. The optical filters can be used to remove the higher order of diffraction from the excitation light beam. The excitation light source module 101 comprises a transceiver 111 connected to the digital communication network 110 and arranged to support the digital communication protocol used in the digital communication network. The digital communication network can be used for transferring control and monitoring data to and from the excitation light source module 101. The control and monitoring data can relate, for example, to timing of generation of the excitation light, electrical power delivered to the excitation light source, and/or the position of the optical filter wheel.

The excitation light source module 101 is coupled to the excitation monocromator module 102 with a light guide 129 that can be e.g. a fiber bundle. The excitation monocromator module 102 operates as an adjustable optical pass-band filter. The excitation monocromator module 102 comprises a transceiver 112 connected to the digital communication network 110 and arranged to support the digital communication protocol used in the digital communication network. The digital communication network can be used for transferring control and monitoring data to and from the excitation monocromator module 102. The control and monitoring data can relate, for example, characteristics of the optical pass-band related to the excitation monocromator module 102.

The excitation monocromator module 102 is coupled with a light guide 134 to the measurement head module 103 that comprises two channels, one for the excitation light beam and another for an emission light beam emitted by the sample 153 being measured. In principle it is possible use the excitation light source 108 for producing excitation light beams for more than one sample being measured simultaneously. For example, the light guide 134 could be replaced with a branched light guide connected to two separate measurement head modules. The measurement head module 103 comprises plano-convex lenses arranged to focus the excitation light beam to the sample being measured and to collect the emission light beam from the sample. The measurement head module is provided with a photodiode detector 132. A part of the excitation beam is scattered from a mirror 133 to the photodiode detector 132. Relative changes in a signal produced by the photodiode detector can be used for correcting adverse effects caused by variation in the output of the excitation light source 108 and by variation in the proper-ties of the optical path from the flash lamp to the measurement head. The signal produced by the photodiode detector 132 is converted into a digital form with an analog-to-digital converter 138. The measurement head module 103 comprises a transceiver 113 connected to the digital communication network 110 and arranged to support the digital communication protocol used in the digital communication network. The digital communication network can be used for transferring control, monitoring, and feedback data to and/or from the measurement head module 103. The feedback data includes digital information based on the signal produced by the photodiode detector 132. A digital circuitry 139 is arranged to provide the digital information with identifier data that identifies, in accordance with the digital communication protocol, from among the operational modules 101, 102, 104, 105, 106 and 107 the particular operational module/modules to which the digital information is to be delivered via the digital communication network, i.e. the identifier data identifies the one or more operational modules that represent destinations of the digital information to be transferred. The identifier data can comprise, for example, the protocol addresses of the one or more destination operational modules. The digital circuitry 139 is preferably arranged to connect one or more protocol addresses of the one or more destination operational modules to the digital information to be transferred. As the signal produced by the photodiode detector 132 is converted into a digital form locally within the measurement head module 103, there is no need to transfer the said signal between different operational modules in a vulnerable analog form.

The emission light beam collected with the measurement head module 103 is guided with a light guide 134 to the emission monocromator module 104 that operates as an adjustable optical pass-band filter. An optical filter wheel 135 is placed at the output of the emission monocromator. Optical filters similar to the optical filters 128 in the excitation side can be used. The emission monocromator module 104 comprises a transceiver 114 connected to the digital communication network 110 and arranged to support the digital communication protocol used in the digital communication network. The digital communication network can be used for transferring control and monitoring data to and from the emission monocromator module 104. The control and monitoring data can relate, for example, characteristics of the optical pass-band related to the emission monocromator module 104 and/or to the position of the optical filter wheel 135.

The emission monocromator module 104 is coupled with a light guide 136 to the detector module 105 that includes a detector 109 arranged to detect the emission beam emitted by the sample 153 and to produce a detection signal responsive to the detected emission beam. The detector 109 is preferably a photomultiplier tube. The detector module 105 comprises an analog-to-digital converter 118 arranged to convert the detection signal produced by the detector 109 into a digital form. The detector module 105 comprises a transceiver 115 connected to the digital communication network 110 and arranged to support the digital communication protocol used in the digital communication network. The digital communication network can be used for transferring control, monitoring, and measurement data to and/or from the detector module 105. The measurement data includes digital information based on the detection signal produced by detector 109. A digital circuitry 119 is arranged to provide the digital information with identifier data that identifies, in accordance with the digital communication protocol, from among the operational modules 101, 102, 103, 104, 106 and 107 the particular operational module/modules to which the digital information is to be delivered via the digital communication network, i.e. the identifier data identifies the one or more operational modules that represent destinations of the digital information. The identifier data can comprise, for example, the protocol addresses of the one or more destination operational modules. The digital circuitry 119 is preferably arranged to connect one or more protocol addresses of the one or more destination operational modules to the said digital information. As the detection signal produced by the detector 109 is converted into a digital form locally within the detector module 105, there is no need to transfer the said detection signal between different operational modules in a vulnerable analog form. The detector module 105 may further comprise a processor (not shown) that is arranged to perform digital signal processing to the digital information based on the detection signal.

The control module 107 is preferably arranged to co-ordinate the operation of the other operational modules 101-106. The control module 107 comprises a transceiver 117 connected to the digital communication network 110 and arranged to support the digital communication protocol used in the digital communication network. The co-ordination of the operation of the operational modules 101-106 can be realized with the aid of control, monitoring and synchronization data transferred via the digital communication network between the control module 107 and the other operational modules 101-106. The control module may comprise a processor device that is arranged to compute measurement results for the samples 151-157 on the basis of the measurement data received from the detector module 105 and the feedback data received from the measurement head module 103. The control module may be further arranged to control a user interface (not shown).

As the operational modules 101-107 are arranged to communicate with each other via the digital communication network 110 using the pre-determined digital communication protocol, the operational modules can be tested independently of each other using an appropriate computer system arranged to support the pre-determined digital communication protocol and to operate as a test bench. This makes, for example, easier to outsource the manufacturing and/or testing of the operational modules 101-107.

An optical measurement instrument according to an embodiment of the invention comprises another digital communication network 120, and two or more of the operational modules 101-107 comprise another transceiver connected to the other digital communication network. The digital communication network 120 can be used for transferring synchronization messages between operational modules. This may be needful if, in the digital communication network 110, data transfer de-lays between operational modules are so long and/or so stochastic that the digital communication network 110 is not suitable for providing sufficiently accurate synchronization between the operational modules. The digital communication network 120 is preferably arranged to use a digital communication protocol that is simpler than that being used in the digital communication network 110. Hence, in the digital communication network 120, it is easier to make the data transfer delays short-er and more deterministic than in the digital communication network 110. A synchronization message transferred in the digital communication network 120 may comprise, for example, a pre-determined bit pattern that represents a timing trigger and another bit pattern that identifies the operational module that is the target of the synchronization message. It is also possible to use the following synchronization principle: a transmitting operational module transmits via the digital communication network 120 data that tells to the receiving operation module that the next or otherwise pre-determined rising or descending signal edge occurring in the digital communication network 120 will act as a triggering event for synchronization. After this, the transmitting operational module makes the rising or descending signal edge in order to achieve synchronization between the transmitting and receiving operational modules. It is also possible that the transmitting operational module transmits via the digital communication network 120, prior or after making the rising or descending signal edge, further data that relates to the synchronization. The further data related to the synchronization may tell to the receiving operational module e.g. that the synchronization is related to operation of a certain particular element of the receiving operation module, e.g. an excitation light source. It is also possible that the transmitting operational module transmits via the digital communication network 120, prior or after making the rising or descending signal edge, other data that is not related to the synchronization. The signal, e.g. signal edge or a pre-determined bit-pattern, which triggers the synchronization of operational modules is preferably processed with hardware means in order to achieve fast and accurate synchronization. In the exemplifying optical measurement instrument illustrated in FIG. 1, the operational modules 101, 103, 105, and 107 comprise transceivers 121, 123, 125, and 127 that are connected to the digital communication network 120.

Figure 2:
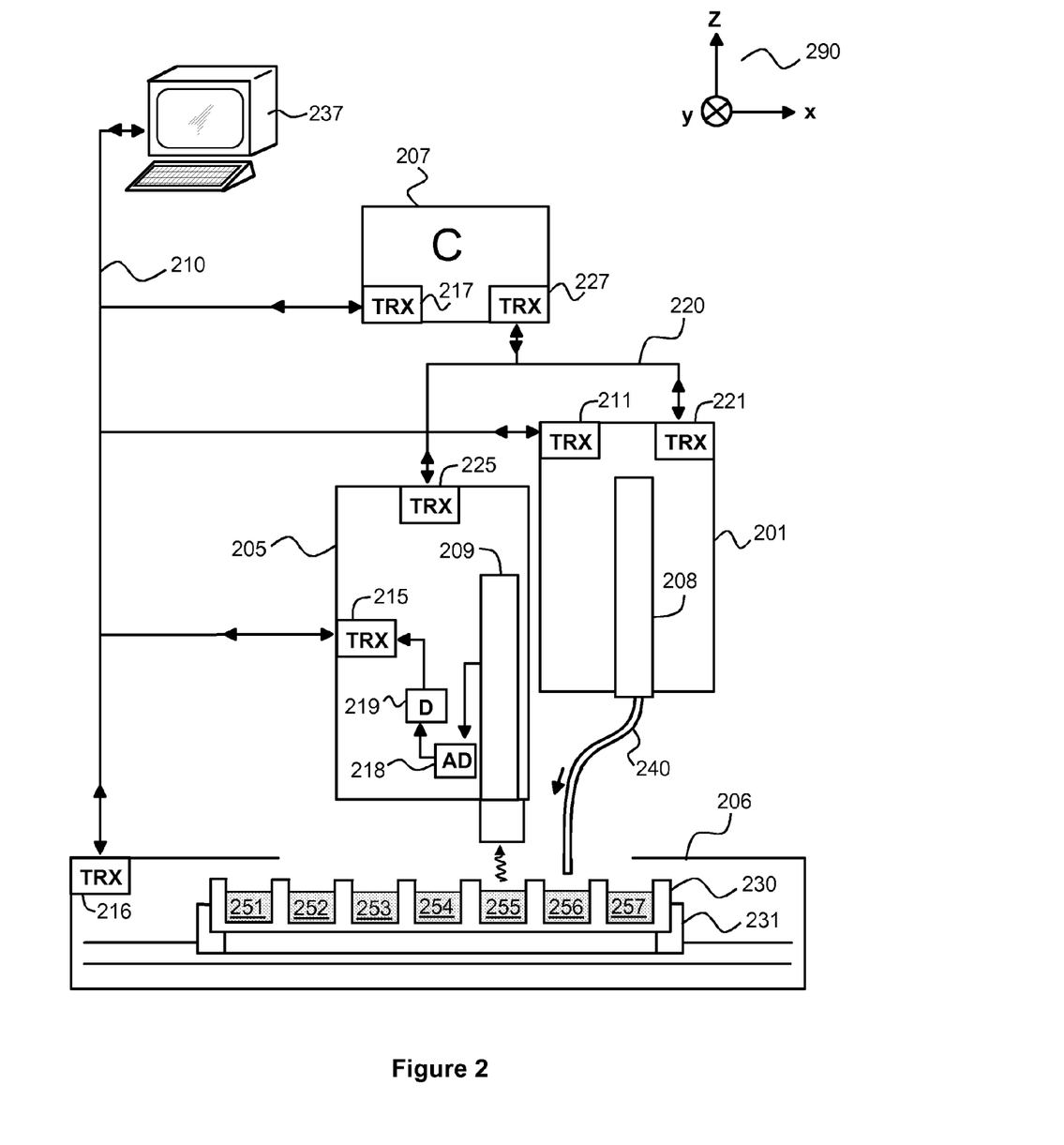
FIG. 2 shows a schematic illustration of an optical measurement instrument according to an embodiment of the invention.

FIG. 2 shows a schematic illustration of an optical measurement instrument according to an embodiment of the invention. The optical measurement instrument is suitable for e.g. the AlphaScreen™ measurements and it comprises the following operational modules: an excitation light source module 201, a sample track module 206, a detector module 205, and a control module 207. The optical measurement instrument comprises at least a part of a digital communication network 210 arranged to support a pre-determined digital communication protocol. The digital communication network 210 may extend outside the optical measurement instrument for example to an external control and/or monitoring system 237.

Samples 251, 252, 253, 254, 255, 256, 257 to be measured are stored in sample wells that are built on a sample plate 230. The sample track module 206 comprises a sledge 231 that is adapted to receive the sample plate and is movable in the xy-plane defined by a co-ordinate system 290. The sample track module 206 comprises a transceiver 216 connected to the digital communication network 210 and arranged to support the digital communication protocol used in the digital communication network.

The excitation light source module 201 comprises an excitation light source 208 that is a laser source, e.g. a 680 nm semiconductor laser. The excitation light produced by the excitation light source is guided to the sample 256 being excited with a light guide 240 that can be e.g. a fiber bundle. The excitation light source module 201 comprises a transceiver 211 connected to the digital communication network 210 and arranged to support the digital communication protocol used in the digital communication network.

The detector module 205 includes a detector 209 arranged to detect the emission beam emitted by the sample 255 being measured and to produce a detection signal responsive to the detected emission beam. The detector 209 is preferably a photomultiplier tube. The detector module 205 comprises an analog-to-digital converter 218 arranged to convert the detection signal produced by the detector 209 into a digital form. The detector module 205 comprises a transceiver 215 connected to the digital communication network 210 and arranged to support the digital communication protocol used in the digital communication network. A digital circuitry 219 is arranged to provide digital information based on the detection signal with identifier data that identifies, in accordance with the digital communication protocol, from among the operational modules 201, 206, and 207 the particular operational module/modules to which the digital information is to be delivered via the digital communication network, i.e. the identifier data identifies the one or more operational modules that represent destinations of the said digital information. The identifier data can comprise, for example, the protocol addresses of the one or more destination operational modules. As the detection signal produced by the detector 209 is converted into a digital form locally within the detector module 205, there is no need to transfer the said detection signal between different operational modules in a vulnerable analog form. The detector module 205 may further comprise a processor (not shown) that is arranged to perform digital signal processing to the digital information based on the detection signal.

The control module 207 is preferably arranged to co-ordinate the operation of the other operational modules 201, 205, and 206. The control module 207 comprises a transceiver 217 connected to the digital communication network 210 and arranged to support the digital communication protocol used in the digital communication network. The co-ordination of the operation of the operational modules 201, 205, and 206 can be realized with the aid of control, monitoring and synchronization data transferred via the digital communication network between the control module 207 and the other operational modules. The control module may comprise a processor device that is arranged to compute measurement results for the samples 251-257 on the basis of the digital information received from the detector module 205. The control module may be further arranged to control a user inter-face (not shown).

An optical measurement instrument according to an embodiment of the invention comprises another digital communication network 220, and two or more of the operational modules 201, 205, 206, and 207 comprise another transceiver connected to the other digital communication network 220. The digital communication network 220 can be used for transferring synchronization messages between operational modules. This may be needful if, in the digital communication network 210, data transfer delays between operational modules are so long and/or so stochastic that the digital communication network 210 is not suitable for providing sufficiently accurate synchronization between the operational modules. The digital communication network 220 is preferably arranged to use a digital communication protocol that is simpler than that being used in the digital communication network 210. In the exemplifying optical measurement instrument illustrated in FIG. 2, the operational modules 201, 205, and 207 comprise transceivers 221, 225, and 227 that are connected to the digital communication network 220.

Figure 3:
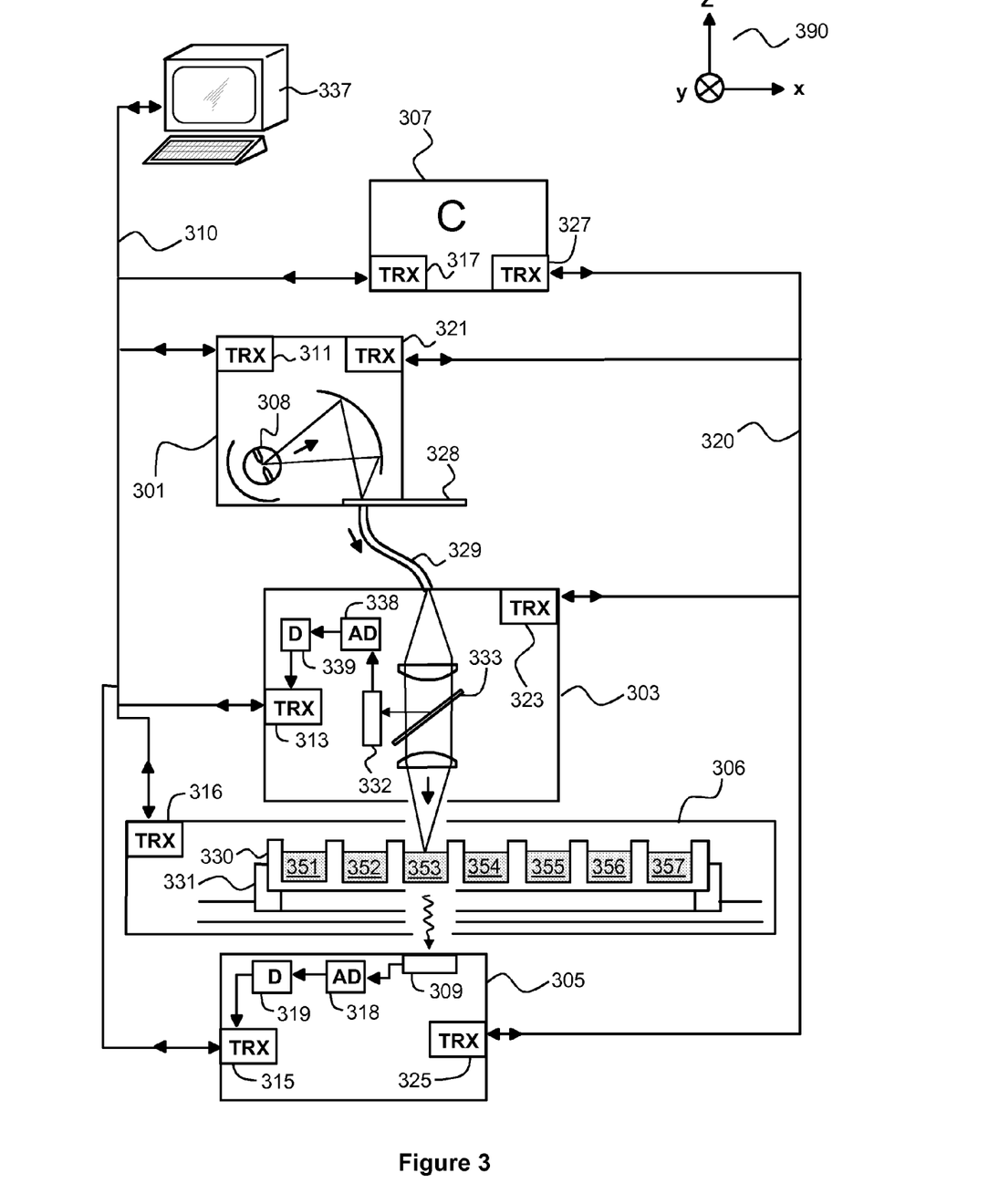
FIG. 3 shows a schematic illustration of an optical measurement instrument according to an embodiment of the invention.

FIG. 3 shows a schematic illustration of an optical measurement instrument according to an embodiment of the invention. The optical measurement instrument is suitable for e.g. absorption measurements and it comprises the following operational modules: an excitation light source module, an excitation module 303, a sample track module 306, a detector module 305, and a control module 307. The optical measurement instrument comprises at least a part of a digital communication network 310 arranged to support a pre-determined digital communication protocol. The digital communication network 310 may extend outside the optical measurement instrument for example to an external control and/or monitoring sys-tem 337.

Samples 351, 352, 353, 354, 355, 356, 357 to be measured are stored in sample wells that are built on a sample plate 330. The sample track module 306 comprises a sledge 331 that is adapted to receive the sample plate and is movable in the xy-plane defined by a co-ordinate system 390. The sample track module 306 comprises a transceiver 316 connected to the digital communication network 310 and arranged to support the digital communication protocol used in the digital communication network.

The excitation light source module 301 comprises an excitation light source 308 that can be for example a flash lamp such as a xenon flash lamp. The excitation light produced by the excitation light source is focused with a concave mirror to an optical filter wheel 328. The excitation light source module 301 comprises a transceiver 311 connected to the digital communication network 310 and arranged to support the digital communication protocol used in the digital communication network.

The excitation light source module 301 is coupled with a light guide 329 to the excitation module 303. In principle it is possible use the excitation light source 308 for producing excitation light beams for more than one sample being measured simultaneously. For example, the light guide 329 could be replaced with a branched light guide connected to two separate excitation modules. The excitation module 303 comprises plano-convex lenses arranged to focus the excitation light beam to the sample 353 being measured. The excitation module is provided with a photodiode detector 332. A part of the excitation beam is scattered from a mirror 333 to the photodiode detector 332. Relative changes in a signal produced by the photodiode detector can be used for correcting adverse effects caused by variation in the output of the excitation light source 308. The signal produced by the photodiode detector 332 is converted into a digital form with an analog-to-digital converter 338. The excitation module 303 comprises a transceiver 313 connected to the digital communication network 310 and arranged to support the digital communication protocol used in the digital communication network. A digital circuitry 339 is arranged to provide digital information based on the signal produced by the photodiode detector 332 with identifier data that identifies, in accordance with the digital communication protocol, from among the operational modules 301, 305, 306 and 307 the particular operational module/modules to which the digital information is to be delivered via the digital communication network, i.e. the identifier data identifies the one or more operational modules that represent destinations of the said digital information. The identifier data can comprise, for example, the protocol addresses of the one or more destination operational modules. As the signal produced by the photodiode detector 332 is converted into a digital form locally within the excitation module 303, there is no need to transfer the said signal between different operational modules in a vulnerable analog form.

The detector module 305 includes a detector 309 arranged to measure absorbance of the sample 353 being measured. The detector is arranged to produce detection signals responsive to a light beam received from the sample 353 being measured and to a light beam received in a corresponding situation but without the sample. The detector 309 is preferably a photodiode. The detector module 305 comprises an analog-to-digital converter 318 arranged to convert the detection signals produced by the detector 309 into a digital form. The detector module 305 comprises a transceiver 315 connected to the digital communication network 310 and arranged to support the digital communication protocol used in the digital communication network. A digital circuitry 319 is arranged to provide digital information based on the detection signals with identifier data that identifies, in accordance with the digital communication protocol, from among the operational modules 301, 303, 306 and 307 the particular operational module/modules to which the digital information is to be delivered via the digital communication network, i.e. the identifier data identifies the one or more operational modules that represent destinations of the said digital information. The identifier data can comprise, for example, the protocol addresses of the one or more destination operational modules. As the detection signals produced by the detector 309 are converted into a digital form locally within the detector module 305, there is no need to transfer the said detection signals between different operational modules in a vulnerable analog form. The detector module 305 may further comprise a processor (not shown) that is arranged to perform digital signal processing to the digital information based on the detection signals.

The control module 307 is preferably arranged to co-ordinate the operation of the other operational modules 301, 303, 305, and 306. The control module 307 comprises a transceiver 317 connected to the digital communication network 310 and arranged to support the digital communication protocol used in the digital communication network. The co-ordination of the operation of the operational modules 301, 303, 305, and 306 can be realized with the aid of control, monitoring and synchronization data transferred via the digital communication network between the control module 307 and the other operational modules. The control module may comprise a processor device that is arranged to compute measurement results for the samples 351-357 on the basis of the digital information received from the detector module 305 and from the excitation module 303. The control module may be further arranged to control a user interface (not shown).

An optical measurement instrument according to an embodiment of the invention comprises another digital communication network 320, and two or more of the operational modules 301, 303, 305, 306, and 307 comprise another transceiver connected to the other digital communication network. The digital communication network 320 can be used for transferring synchronization messages between operational modules. This may be needful if, in the digital communication network 310, data transfer delays between operational modules are so long and/or so stochastic that the digital communication network 310 is not suitable for providing sufficiently accurate synchronization between the operational modules. In the exemplifying optical measurement instrument illustrated in FIG. 3, the operational modules 301, 303, 305 and 307 comprise transceivers 321, 323, 325, and 327 that are connected to the digital communication network 320.

Referring to FIGS. 1, 2 and 3, an operational module according to an embodiment of the invention comprises:

a detector 109, 209, 309 arranged to detect an emission beam emitted by one of samples to be measured and to produce a detection signal responsive to the detected emission beam, an analog-to-digital converter 118, 218, 318 arranged to convert the detection signal into a digital form, a digital circuitry 119, 219, 319 arranged to provide digital information based on the detection signal with identifier data arranged to identify another operational module to which the digital information is to be delivered, and a transceiver 115, 215, 315 arranged to transmit, according to a digital communication protocol, the digital information provided with the identifier data.

In an operational module according to an embodiment of the invention, the transceiver 115, 215, 315 is arranged to support a Controller Area Network (CAN).

In an operational module according to an embodiment of the invention, the transceiver 115, 215, 315 is arranged to support the Ethernet communication protocol.

In an operational module according to an embodiment of the invention, the detector 109, 209, 309 comprises at least one of the following: a photomultiplier tube, a photodiode.

An operational module according to an embodiment of the invention comprises another transceiver 125, 225, 325 for transferring and receiving synchronization messages to and from other operational modules.

Figure 4:
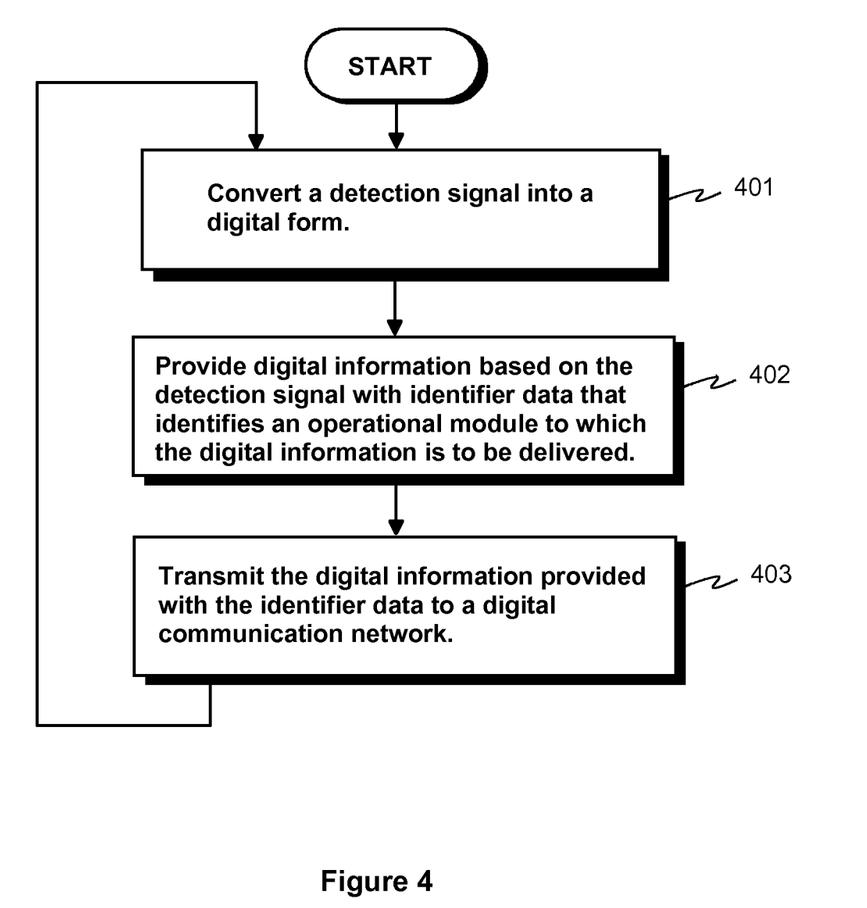
FIG. 4 shows a flow chart of a method according to an embodiment of the invention for transferring information between operational modules of an optical measurement instrument.

FIG. 4 shows a flow chart of a method according to an embodiment of the invention for transferring information between operational modules of an optical measurement instrument. At least one of the operational modules includes an excitation light source arranged to produce an excitation beam for at least one of samples to be measured, and at least one of the operational modules includes a detector arranged to detect an emission beam emitted by one of the samples to be measured and to produce a detection signal responsive to the detected emission beam. The method comprises the following actions in the at least one operational module in which the detection signal is produced:

converting, in the phase 401, the detection signal into a digital form, providing, in the phase 402, digital information based on the detection signal with identifier data that identifies from among the operational modules the particular operational module to which the digital information is to be delivered, and transmitting, in the phase 403, the digital information provided with the identifier data to a digital communication network connected to the operational modules and arranged to support a pre-determined digital communication protocol.

A method according to an embodiment of the invention further comprises transferring a synchronization message from one of the operational modules to another of the operational modules using another communication network connected to the operational modules.

In a method according to an embodiment of the invention, the digital communication network is a Controller Area Network (CAN).

The specific examples provided in the description given above should not be construed as limiting. Therefore, the invention is not limited merely to the embodiments described above.

What is claimed is:

1. An optical measurement instrument comprising:

operational modules (101-107, 201, 205, 206, 207, 301, 303, 305, 306, 307), at least one of the operational modules including an excitation light source (108, 208, 308) arranged to produce an excitation beam for at least one of samples (151-157, 251-257, 351-357) to be measured, and at least one of the operational modules including a detector (109, 209, 309) arranged to detect an emission beam emitted by one of the samples to be measured and to produce a detection signal responsive to the detected emission beam, at least a part of a digital communication network (110, 210, 310) arranged to support a digital communication protocol, wherein:
each of the operational modules comprises a transceiver (111-117, 211, 215, 216, 217, 311, 313, 315, 316, 317) connected to the digital communication network and arranged to support the digital communication protocol, and the at least one operational module that includes a detector further comprises an analog-to-digital converter (118, 218, 318) arranged to convert the detection signal into a digital form and a digital circuitry (119, 219, 319) arranged to provide digital information based on the detection signal with identifier data arranged to identify from among the operational modules the particular operational module to which the digital information is to be delivered via the digital communication network, characterized in that the optical measurement instrument further comprises another digital communication network (120, 220, 320) and at least two of the operational modules comprise another transceiver (121, 123, 125, 127, 221, 225, 227, 321, 323, 325, 327) connected to the other digital communication network for transferring synchronization messages between the at least two operational modules.

2. An optical measurement instrument according to claim 1, wherein the digital communication network is a Controller Area Network (CAN).

3. An optical measurement instrument according to claim 1, wherein the digital communication network is an Ethernet network.

4. An optical measurement instrument according to claim 1, comprising at least the following operational modules: an excitation light source module (101) including a flash lamp, an excitation monocromator module (102), a measurement head module (103), a sample track module (106) arranged to hold and move a sample plate, an emission monocromator module (104), and a detector module (105) including a photomultiplier tube.

5. An optical measurement instrument according to claim 1, comprising at least the following operational modules: an excitation light source module (201) including a laser source, a sample track module (206) arranged to hold and move a sample plate, and a detector module (205) including a photomultiplier tube.

6. An optical measurement instrument according to claim 1, comprising at least the following operational modules: an excitation light source module (301) including a flash lamp, a excitation module (303), a sample track module (306) arranged to hold and move a sample plate, and a detector module (305) including a photodiode arranged to measure absorbance of the sample being measured.

7. An optical measurement instrument according to claim 1, wherein one of the at least two operational modules is arranged to transmit via the other digital communication network (120) data arranged to tell to another of the at least two operational modules that a pre-determined rising or descending signal edge that will occur in the other digital communication network (120) will act as a triggering event for synchronization of the at least two operational modules, and subsequently to make the rising or descending signal edge in order to achieve the synchronization between the at least two operational modules.

8. An operational module (105, 205, 305) for an optical measurement instrument, the operational module comprising:
a detector (109, 209, 309) arranged to detect an emission beam emitted by one of samples to be measured and to produce a detection signal responsive to the detected emission beam,
an analog-to-digital converter (118, 218, 318) arranged to convert the detection signal into a digital form,
a digital circuitry (119, 219, 319) arranged to provide digital information based on the detection signal with identifier data arranged to identify another operational module to which the digital information is to be delivered, and
a transceiver (115, 215, 315) arranged to transmit, according to a digital communication protocol, the digital information provided with the identifier data, characterized in that the operational module further comprises another transceiver (125, 225, 325) for transferring and receiving synchronization messages to and from other operational modules.

9. An operational module according to claim 8, wherein the transceiver is arranged to support a Controller Area Network (CAN).

10. An operational module according to claim 8, wherein the transceiver is arranged to support Ethernet communication protocol.

11. An operational module according to claim 8, wherein the detector comprises at least one of the following: a photomultiplier tube, a photodiode.

12. A method for transferring information between operational modules of an optical measurement instrument, at least one of the operational modules including an excitation light source arranged to produce an excitation beam for at least one of samples to be measured, and at least one of the operational modules including a detector arranged to detect an emission beam emitted by one of the samples to be measured and to produce a detection signal responsive to the detected emission beam, the method comprising in the at least one operational module in which the detection signal is produced:
converting (401) the detection signal into a digital form,
providing (402) digital information based on the detection signal with identifier data that identifies from among the operational modules the particular operational module to which the digital information is to be delivered, and
transmitting (403) the digital information provided with the identifier data to a digital communication network connected to the operational modules and arranged to support a digital communication protocol, characterized in that the method further comprises transferring a synchronization message from one of the operational modules to another of the operational modules using another communication network connected to the operational modules.

13. A method according to claim 12, wherein the digital communication network is a Controller Area Network (CAN).

* * * * *